(12) United States Patent
Yasukawa et al.

(10) Patent No.: US 8,088,945 B2
(45) Date of Patent: Jan. 3, 2012

(54) PALLADIUM-CONTAINING CATALYST, METHOD FOR PRODUCING SAME, AND METHOD FOR PRODUCING α,β-UNSATURATED CARBOXYLIC ACID

(75) Inventors: Toshiya Yasukawa, Hiroshima (JP); Toshiki Matsui, Hiroshima (JP); Ken Ooyachi, Hiroshima (JP); Yoshiyuki Himeno, Hiroshima (JP); Wataru Ninomiya, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 12/965,509

(22) Filed: Dec. 10, 2010

(65) Prior Publication Data

US 2011/0082315 A1 Apr. 7, 2011

Related U.S. Application Data

(62) Division of application No. 11/816,584, filed as application No. PCT/JP2006/302795 on Feb. 17, 2006, now abandoned.

(30) Foreign Application Priority Data

| Feb. 18, 2005 | (JP) | 2005-042494 |
| Mar. 4, 2005 | (JP) | 2005-060545 |
| Nov. 11, 2005 | (JP) | 2005-327362 |

(51) Int. Cl.

| C07C 51/14 | (2006.01) |
| C07C 51/16 | (2006.01) |
| C07C 51/235 | (2006.01) |
| C07C 249/00 | (2006.01) |
| C07C 251/00 | (2006.01) |
| C07C 259/00 | (2006.01) |
| C07C 291/00 | (2006.01) |
| B01J 23/00 | (2006.01) |
| B01J 23/42 | (2006.01) |
| B01J 23/44 | (2006.01) |

(52) U.S. Cl. ........ 562/522; 562/533; 562/546; 502/325; 502/339; 502/353; 558/446; 558/470

(58) Field of Classification Search .............. 502/325, 502/339, 353; 562/522, 533, 546; 558/446, 558/470

See application file for complete search history.

(56) References Cited

U.S. PATENT DOCUMENTS

| 4,225,727 A | 9/1980 | Kamiyama et al. |
| 4,456,555 A | 6/1984 | Goel et al. |
| 5,283,379 A | 2/1994 | Saiki et al. |
| 6,407,280 B1 | 6/2002 | Chaturvedi et al. |
| 6,514,901 B1 | 2/2003 | Lin et al. |
| 7,026,502 B2 | 4/2006 | Benderly et al. |
| 7,446,223 B2 | 11/2008 | Ninomiya et al. |
| 7,884,239 B2* | 2/2011 | Fujimori et al. ............ 562/532 |
| 7,994,091 B2* | 8/2011 | Himeno et al. ............ 502/339 |
| 2010/0323879 A1* | 12/2010 | Yamada et al. ............ 502/27 |

FOREIGN PATENT DOCUMENTS

| CN | 1326378 A | 12/2001 |
| CN | 1500073 A | 5/2004 |
| JP | 56 59722 | 5/1981 |
| JP | 4 118051 | 4/1992 |
| JP | 4 210937 | 8/1992 |
| JP | 10 7616 | 1/1998 |
| JP | 10 263399 | 10/1998 |
| JP | 2004 141863 | 5/2004 |
| WO | 2005/118134 | 12/2005 |

OTHER PUBLICATIONS

Office Action issued Aug. 10, 2010, in Indian Patent Application No. 4102/CHENP/2007.

Office Action issued Jun. 15, 2011, in Chinese Patent Application No. 200910139818.0 with partial English translation.

* cited by examiner

*Primary Examiner* — Patricia L Hailey

(74) *Attorney, Agent, or Firm* — Oblon, Spivak, McClelland, Maier & Neustadt, L.L.P.

(57) ABSTRACT

Disclosed is a palladium-containing catalyst which enables to produce an α,β-unsaturated carboxylic acid in high selectivity from an olefin or an α,β-unsaturated aldehyde. Also disclosed are a method for producing such a catalyst and a method for producing an α,β-unsaturated carboxylic acid using such a catalyst. Specifically disclosed is a palladium-containing catalyst containing 0.001 to 0.25 mole of antimony element to 1 mole of palladium element or a palladium-containing catalyst containing palladium element which composes a metal, tellurium element, and bismuth element.

2 Claims, No Drawings

PALLADIUM-CONTAINING CATALYST, METHOD FOR PRODUCING SAME, AND METHOD FOR PRODUCING α,β-UNSATURATED CARBOXYLIC ACID

TECHNICAL FIELD

The present invention relates to a method for producing a palladium-containing catalyst to produce an α, β-unsaturated carboxylic acid from an olefin or an α, β-unsaturated aldehyde, and a method for producing the palladium-containing catalyst, and a method for producing the α, β-unsaturated carboxylic acid.

BACKGROUND ART

There are many industrially useful materials among α, β-unsaturated carboxylic acids. For example, acrylic acid and methacrylic acid are quite largely used for raw materials of synthetic resins and the like.

As a method for producing an α, β-unsaturated carboxylic acid, a method of liquid-phase oxidation of an olefin or an α,β-unsaturated aldehyde with molecular oxygen has been researched. As a catalyst for producing the α, β-unsaturated carboxylic acid through liquid-phase oxidation of the olefin or the α, β-unsaturated aldehyde with molecular oxygen, for example, a palladium-containing catalyst is proposed in Patent Document 1. Further, as the catalyst for producing the α, β-unsaturated carboxylic acid through liquid-phase oxidation of the olefin with molecular oxygen, a palladium-containing catalyst which contains an intermetallic compound between palladium and lead, bismuth, thallium or mercury is proposed in Patent Document 2.

As a palladium-containing catalyst suitable for producing benzyl acetate, though not for producing a carboxylic acid, a catalyst having an atomic ratio of palladium/bismuth being 3/1.4 to 3/0.8 for producing a carboxylic acid ester is proposed in Patent Document 3. A catalyst having an atomic ratio of palladium/bismuth being 2.5 to 3.5 for producing benzyl acetate is proposed in Patent Document 4.

Patent Document 1: Japanese Patent Application Laid-Open No. 2004-141,863
Patent Document 2: Japanese Patent Application Laid-Open No. Sho 56-59,722
Patent Document 3: Japanese Patent Application Laid-Open No. Hei 10-263,399
Patent Document 4: Japanese Patent Application Laid-Open No. Hei 10-7,616

DISCLOSURE OF INVENTION

Problem to be Solved by the Invention

However, selectivities to the target α, β-unsaturated carboxylic acid in a liquid-phase oxidation using the palladium-containing catalysts described in Patent Documents 1 and 2 were not sufficient and a further improvement of the selectivity has been desired. Further, when the catalysts described in Patent Documents 3 and 4 were used as a substitute for the catalyst for producing the α, β-unsaturated carboxylic acid through liquid-phase oxidation of the olefin or the α, β-unsaturated aldehyde with molecular oxygen, the selectivities to the α, β-unsaturated carboxylic acid were, in many cases, not high.

Further, in the liquid-phase oxidations using the foregoing catalysts, a large amount of carbon dioxide was formed as a by-product. Consequently, a catalyst which can suppress the selectivity to carbon dioxide has been desired because the selectivity to the α, β-unsaturated carboxylic acid was lowered as the selectivity to carbon dioxide became high.

Therefore, it is an object of the present invention to provide a palladium-containing catalyst which enables to produce an α, β-unsaturated carboxylic acid in high selectivity from an olefin or an α, β-unsaturated aldehyde. It is another object of the present invention to provide a method for producing such a catalyst. It is also another object of the present invention to provide a method for producing an α, β-unsaturated carboxylic acid using such a catalyst.

Means For Solving The Problem

One aspect of the present invention is a palladium-containing catalyst for producing an α, β-unsaturated carboxylic acid from an olefin or an α, β-unsaturated aldehyde, in which the palladium-containing catalyst is either the following (i) or the following (ii).

(i) a palladium-containing catalyst including 0.001 to 0.25 mole of antimony element to 1 mole of palladium element, (ii) a palladium-containing catalyst including palladium element which composes a metal, tellurium element, and bismuth element.

The palladium-containing catalyst of the foregoing (i) may further include 0.001 to 0.4 mole of tellurium element to 1 mole of palladium element. The palladium-containing catalyst of the foregoing (i) can be produced by a method comprising the steps of reducing a compound containing palladium element in an oxidized state with a reducing agent, and reducing a compound containing antimony element in an oxidized state with a reducing agent.

The palladium-containing catalyst of the foregoing (ii) can be produced by a method comprising the step of reducing a compound containing palladium element in an oxidized state, a compound containing tellurium element in an oxidized state, and a compound containing bismuth element in an oxidized state with a reducing agent.

Further, another aspect of the present invention is a method for producing an α, β-unsaturated carboxylic acid, comprising the step of:

carrying out oxidation of an olefin or an α, β-unsaturated aldehyde with molecular oxygen in a liquid-phase using the foregoing palladium-containing catalyst.

Effect of the Invention

According to the present invention, a palladium-containing catalyst which enables to produce an α, β-unsaturated carboxylic acid in high selectivity from an olefin or an α, β-unsaturated aldehyde can be provided. Further, the α, β-unsaturated carboxylic acid can be produced in high selectivity by using the palladium-containing catalyst. Further, a formation of carbon dioxide which is a by-product can be reduced.

BEST MODE FOR CARRYING OUT THE INVENTION

The palladium-containing catalyst of the present invention (hereinafter, also abbreviated to "catalyst") is a catalyst for producing the α, β-unsaturated carboxylic acid through liquid-phase oxidation of the olefin or the α, β-unsaturated aldehyde with molecular oxygen (hereinafter, also abbreviated to "liquid-phase oxidation").

(The First Embodiment of The Palladium-Containing Catalyst)

The first embodiment of the palladium-containing catalyst of the present invention is the one comprising 0.001 to 0.25 mole of antimony element to 1 mole of palladium element. It is preferable that the catalyst further comprise 0.001 to 0.4 mole of tellurium element to 1 mole of palladium element.

It is preferable that palladium element contained in the catalyst be in a metallic state of 0 valence sate. It is preferable that antimony element contained in the catalyst be in an oxidized state of +3, +4, or +5 valence state, or in a metallic state of 0 valence state. It is preferable that tellurium element contained in the catalyst in some cases be in an oxidized state of +6 or +4 valence state, or in a metallic state of 0 valence state.

The catalyst becomes capable of producing the $\alpha$, $\beta$-unsaturated carboxylic acid in high selectivity from the olefin or the $\alpha$, $\beta$-unsaturated aldehyde by adjusting the number of moles of antimony element to 1 mole of palladium element in the catalyst (namely, molar ratio of antimony element to palladium element: Sb/Pd) to a predetermined range. The Sb/Pd is preferably 0.005 to 0.25 and more preferably 0.01 to 0.23. Further, the catalyst becomes capable of producing the $\alpha$, $\beta$-unsaturated carboxylic acid in higher selectivity from the olefin or the $\alpha$, $\beta$-unsaturated aldehyde by adjusting the number of moles of tellurium element to 1 mole of palladium element in the catalyst (namely, molar ratio of tellurium element to palladium element: Te/Pd) to a predetermined range. The Te/Pd is preferably 0.005 to 0.35 and more preferably 0.01 to 0.3. The Sb/Pd and Te/Pd are adjustable by a compounding ratio of a palladium compound, an antimony compound, and tellurium compound to be used in the production of the palladium-containing catalyst and the like.

The Sb/Pd can be calculated from masses and atomic weights of antimony element and palladium element contained in the catalyst. The masses of antimony element and palladium element contained in the catalyst can be quantitatively determined by elemental analysis. Further, in the case that the catalyst is produced by a method like pore-filling method in which substantially the whole amounts of palladium element and antimony element contained in raw materials of palladium and antimony are contained in the catalyst, masses of both the elements may be calculated from a palladium content and a compounding amount of the raw material of palladium to be used and a antimony content and a compounding amount of the raw material of antimony to be used. The Te/Pd can be quantitatively determined by the same method.

As the method for quantitatively determining the masses of palladium element and antimony element in the catalyst by elemental analysis, a method in which the following treatment A liquid and treatment B liquid are prepared and analyzed can be listed. Mass of tellurium element can be measured in the same way.

Preparation of a Treatment A Liquid:

Into a Teflon (registered trademark) decomposition tube, 0.2 g of the catalyst and predetermined amounts of concentrated nitric acid, concentrated sulfuric acid, and hydrogen peroxide aqueous solution are introduced, and a dissolving treatment is carried out using a microwave digestion device (MARS5(trade name) manufactured by CEM Corporation). The resultant sample is filtrated and a filtrate and washing water after used in washing are gathered and filled up to a calibration mark on a measuring flask to make a treatment A liquid.

Preparation of a Treatment B Liquid:

A filter paper on which the insoluble residue of the treatment A liquid has been gathered is transferred into a platinum crucible and it is heated and burnt to ashes, and lithium metaborate is added to it and fused with a gas burner. After cooled, hydrochloric acid and a small amount of water are added to the crucible, and after the fused material is dissolved, the resultant solution is filled up to a calibration mark on a measuring flask to make a treatment B liquid.

Each mass of antimony element and palladium element contained in the treatment A liquid thus obtained and the treatment B liquid thus obtained is determined quantitatively with ICP atomic emission spectrometer (IRIS-Advantage (trade name) manufactured by Thermo Elemental Co., Ltd.), and the mass of each element in the catalyst can be obtained from a sum of masses of each element in both the liquids.

Further, the catalyst of the present invention mentioned above may be a nonsupported type, however, it is preferably a supported type in which palladium element and antimony element, or palladium element, antimony element, and tellurium element are supported on a carrier. As the carrier, for example, activated carbon, carbon black, silica, alumina, magnesia, calcia, titania or zirconia can be listed. Among them, silica, alumina, magnesia, calcia, titania or zirconia is more preferable, and silica, titania or zirconia is particularly preferable. The carrier can be used alone or two or more kinds of these carriers can be used. As the case of two or more kinds of these carriers are used, for example, a mixture such as a mixed oxide obtained by mixing silica and alumina, and a complex oxide such as silica-alumina which is a complex oxide can be listed.

A preferable specific surface area of the carrier cannot be absolutely affirmed because it is variable depending on a kind of carrier and the like. In the case of silica, the specific surface area is preferably 50 $m^2/g$ or more and more preferably 100 $m^2/g$ or more, and preferably 1,500 $m^2/g$ or less and more preferably 1,000 $m^2/g$ or less. As the specific surface area of the carrier becomes smaller, a catalyst in which its useful components (palladium element, antimony element) are supported more on its surface can be produced, and as the specific surface area of the carrier becomes larger, a catalyst in which its useful components are supported more can be produced.

The pore volume of the carrier is not particularly limited, however, it is preferably 0.1 cc/g or more and more preferably 0.2 cc/g or more, and preferably 2.0 cc/g or less and more preferably 1.5 cc/g or less.

The shape or size of the carrier is variable depending on the shape or size of a reactor and not particularly limited, and for example, various shapes such as powder, particle, sphere, and pellet can be listed. Among them, particle and sphere which can be easily operated in filtration and the like are preferable. In the case that the carrier is powder or particle, the particle diameter (median diameter) is preferably 0.5 μm or more and more preferably 1.0 μm or more, and preferably 200 μm or less and more preferably 100 μm or less. As the particle diameter of the carrier becomes larger, separation of a catalyst and a reaction liquid becomes easier, and as the particle diameter of the carrier becomes smaller, dispersibility of the catalyst in the reaction liquid becomes better.

In the case of a supported type catalyst, a total loading ratio of palladium element and antimony element to a carrier is preferably 0.1 to 40% by mass to the mass of the carrier before these elements are supported, more preferably 0.5 to 30% by mass, and furthermore preferably 1.0 to 20% by mass.

A loading ratio in the case of a supported type catalyst can be calculated from the mass of each element obtained by the foregoing method and the like and the mass of the carrier to be used. Further, the mass of the carrier can also be quantitatively determined by the following method. Namely, the catalyst is transferred into a platinum crucible and fused after sodium carbonate is added. To the resultant mixture, distilled water is added to make a homogeneous solution and a quantitative determination of a specific element in the resultant solution is carried out with ICP atomic emission spectrometry. For example, in the case of silica carrier, Si element is quantitatively determined.

The catalyst of the present invention may contain another metal element other than palladium element, antimony element, and tellurium element. As the other metal element, for example, platinum, rhodium, ruthenium, iridium, gold, silver, osmium, copper, lead, bismuth, thallium, or mercury can be listed. One kind or two or more kinds of the other metal elements can be included. From the viewpoint of realizing high catalyst activity, the total amount of palladium element, antimony element, and tellurium element among the metal elements contained in the catalyst is preferably 60% by mass or more and more preferably 80% by mass or more.

The method for producing the catalyst of the present invention will be explained.

The catalyst of the present invention can be suitably produced by a method having a step of reducing a compound containing palladium element in its oxidized state by a reducing agent (hereinafter, also expressed as "Pd reducing step") and a step of reducing a compound containing antimony element in its oxidized state by a reducing agent (hereinafter, also expressed as "Sb reducing step"). In the case of producing the catalyst further containing tellurium element, the catalyst of the present invention can be suitably produced by a method having the Pd reducing step, the Sb reducing step, and a step of adding a compound containing tellurium element (hereinafter, also expressed as "Te adding step"). A step of reducing the compound containing tellurium element may also be carried out after the Te adding step.

As the palladium compound containing palladium element in its oxidized state (hereinafter, also expressed as "raw Pd"), for example, a palladium salt, a palladium oxide, or a palladium oxide alloy can be listed, and among them, the palladium salt is preferable. As the palladium salt, for example, palladium chloride, palladium acetate, palladium nitrate, palladium sulfate, tetraamminepalladium chloride, or palladium bis(acetylacetonate) can be listed, and among them, palladium chloride, palladium acetate, palladium nitrate, or tetraamminepalladium chloride is preferable.

As the antimony compound containing palladium element in its oxidized state (hereinafter, also expressed as "raw Sb"), for example, an antimony salt, antimony alkoxide, metaantimonic acid or its salt, an organic antimony compound, or an antimony oxide can be listed. As the antimony salt, for example, antimony fluoride, antimony chloride, antimony bromide, antimony iodide, antimony acetate, potassium antimonyl tartrate, antimony tartrate, or antimony sulfide can be listed. As the antimony alkoxide, for example, antimony methoxide, antimony ethoxide, antimony isopropoxide, antimony butoxide, or antimony ethylene glycoxide can be listed. As the metaantimonic acid salt, for example, ammonium metaantimonate can be listed. As the organic antimony compound, for example, triphenyl antimony can be listed. Among them, antimony tartrate, ammonium metaantimonate, or the like is preferable.

As the tellurium compound containing tellurium element (hereinafter, also expressed as "raw Te"), tellurium metal, a tellurium salt, telluric acid or its salt, tellurous acid or its salt, a tellurium oxide, or the like can be listed. As the tellurium salt, for example, hydrogen telluride, tellurium tetrachloride, tellurium dichloride, tellurium hexafluoride, tellurium tetraiodide, tellurium tetrabromide, or tellurium dibromide can be listed. As the tellurate, for example, sodium tellurate or potassium tellurate can be listed. As the tellurite, for example, sodium tellurite or potassium tellurite can be listed. Among them, telluric acid or its salt, tellurous acid or its salt, or a tellurium oxide is preferable. Tellurium element contained in the raw Te may be in its oxidized state, reduced state, or metallic state because reduction of the raw Te is not necessarily indispensable.

Further, it is possible to use a compound containing two or more kinds of palladium element, antimony element, and tellurium element as a raw material of the catalyst, other than the method of using the foregoing compounds. Concretely, for example, a palladium-tellurium complex $PdX_n(TeRR')_{4-n}$ can be listed. In the $PdX_n(TeRR')_{4-n}$, Pd represents palladium, X represents fluorine, chlorine, brome, or iodine, Te represents tellurium, and each of R and R' independently represents an alkyl group, and n represents an integer of 0 to 3. Further, it is also possible to use a compound containing both of palladium element in its oxidized state and antimony element in its oxidized state.

The foregoing raw Pd and raw Sb are properly selected and used as the raw materials for producing the catalyst. The compounding amounts of these compounds are properly selected so that an Sb/Pd and loading ratios become predetermined values. In the case of producing a catalyst containing tellurium element, the foregoing raw Te is properly selected and used as the raw material for producing the catalyst. The compounding amount of the raw Te is properly selected so that a Te/Pd and loading ratios become predetermined values.

Further, in the case of producing a catalyst containing another metal element other than palladium element, antimony element, and tellurium element, a compound containing the other metal element (hereinafter, also expressed as "another raw material") may be simultaneously used. As "another raw material", for example, a metal, a metal oxide, a metal salt, a metal oxoacid, and a metal oxoacid salt, which contains the other metal element, can be listed.

A Pd reduction step and an Sb reduction step may be carried out simultaneously or separately. When the respective reduction steps are carried out separately, the order of the Pd reduction step and the Sb reduction step is arbitrary. In the case that a Te adding step is carried out, the Te adding step can be carried out simultaneously with the Pd reduction step and/or the Sb reduction step, or can be carried out in an arbitrary order. Further, in the case that a catalyst containing another metal element other than palladium element, antimony element, and tellurium element is produced and a step of reducing "another raw material" in its oxidized state with a reducing agent is carried out, the reducing step can be carried out simultaneously with the Pd reduction step, and/or the Sb reduction step, and/or Te adding step, or can be carried out in an arbitrary order.

In the case of producing a supported type catalyst, it is preferable to carry out the foregoing reduction step in the presence of a carrier. As a method of reduction at the time of producing the supported type catalyst, for example, (1) a method in which a raw material containing a metal element in its oxidized state is first supported on a carrier and then the metal element is reduced by bringing the resultant carrier into contact with a reducing agent;

(2) a method in which a reducing agent is brought into contact with a solution or slurry which includes a raw material containing a metal atom in its oxidized state, while the solution or slurry is in contact with a carrier, and thereby the metal element is, at the same time, reduced and supported on the carrier; and (3) a method in which the other metal raw material is added after the method (2) is carried out; can be listed. Among them, the reduction method (1) is preferable because a catalyst having high dispersion of metal elements is easily obtainable.

As the reduction method (1), a method in which firstly a carrier is impregnated with a solution in which one kind or two or more kinds of a raw Pd, a raw Sb, a raw Te, and "another raw material" (hereinafter, collectively also expressed as "metal raw materials") are dissolved in a solvent, and secondly the resultant system is subjected to heat treatment to change the metal raw materials into metal oxides, and then the metal oxides is reduced by bringing the metal oxides supported on the carrier into contact with a reducing agent is preferable. Further, in this method, it is also possible to separately provide a step in which the metal raw materials are supported on the carrier by evaporating the solvent previous to the heat treatment.

In the method of producing the catalyst by impregnating the solution to the carrier, a method in which the solvent is evaporated after the carrier is soaked into the solution or a method, what is called pore-filling method, in which the solvent is evaporated after an amount of the solution equivalent to the pore volume of the carrier is absorbed in the carrier is preferable. The solvent of the solution is not particularly limited as long as it can dissolve the metal raw materials. As the solvent for the metal raw materials, for example, water; an organic carboxylic acid such as acetic acid or valeric acid; an inorganic acid such as nitric acid or hydrochloric acid; an alcohol such as ethanol, 1-propanol, 2-propanol, n-butanol or t-butanol; a ketone such as acetone, methyl ethyl ketone, methyl isobutyl ketone or cyclohexanone; a hydrocarbon such as heptane, hexane or cyclohexane can be listed. The solvent can be used alone or in combination of a plurality of these solvents. As the solvent, water or the organic carboxylic acid is preferable from the viewpoint of solubility of the metal raw materials and the reducing agent or dispersibility of the carrier.

As an operation of impregnation of the solution to the carrier, it is possible to carry out the operation only once using the solution containing all the metal raw materials, however, it is also possible to carry out the operations in a plurality of times using a plurality of the solutions. In the case of carrying out the operations in a plurality of times, each operation of impregnation after the first one may be carried out after any one of evaporation of the solvent, heat treatment, or reduction of the preceding operation. The order of supporting the metal elements is not particularly limited.

A temperature of the heat treatment is preferably a decomposition temperature at which the metal raw materials change into metal oxides or above. A temperature of the heat treatment may be the time which is sufficient for at least one part of the metal raw materials to change into metal oxides and is preferably 1 to 12 hours.

As the reduction method (2), for example, a method in which one kind or two or more kinds of the metal raw materials are reduced by bringing a reducing agent into contact with a solution or slurry in which the metal raw materials are dissolved or dispersed, while the solution or slurry is impregnated to a carrier, or a method in which the metal raw materials are reduced by bringing the reducing agent into contact with the foregoing solution or slurry while the carrier is dispersed in the solution or slurry can be listed.

As an operation of bringing the reducing agent into contact with the system to be reduced, it is possible to carry out the operation only once using the solution containing all the metal raw materials, however, it is also possible to carry out the operations in a plurality of times using a plurality of the solutions. In the case of carrying out the operations in a plurality of times, in each reducing treatment after the first one, the carrier subjected to the reducing treatment in the preceding reducing treatment is used. The order of supporting the metal elements is not particularly limited.

As the reduction method (3), for example, a method in which a solution or slurry in which the other metal raw material is separately dissolved or dispersed in a solvent such as water is added to the solution or slurry existing after the metal raw materials are reduced with the reducing agent in the presence of the carrier is preferable. As the solvent for the solution or slurry to be added, water is preferable, however, various organic solvents as mentioned above may be used. A reducing agent may be added again after the addition of the other metal raw material.

In the case of carrying out the reducing treatments in a plurality of times, a kind of a reducing agent, a reducing temperature and reducing time, or a kind of solvent in the case of carrying out the reducing treatments in a liquid phase can be properly set at each time independently.

In the present invention, it is preferable to reduce the raw Pd at first by bringing a reducing agent into contact with a solution of the raw Pd while the solution of the raw Pd and the carrier are in contact with each other, and then to add to the resultant system a solution in which the raw Sb (and the raw Te) is dissolved in water or a slurry in which the raw Sb (and the raw Te) is dispersed in water. Subsequently, the raw Sb (and the raw Te) can be reduced, when it is needed.

The reducing agent to be used in the reduction is not particularly limited, and for example, hydrazine, formaldehyde, sodium borohydride, hydrogen, formic acid, a formic acid salt, ethylene, propylene, 1-butene, 2-butene, isobutylene, 1,3-butadiene, 1-heptene, 1-hexene, 2-hexene, cyclohexene, allyl alcohol, methacryl alcohol, acrolein, or methacrolein can be listed. Among them, hydrazine, formaldehyde, hydrogen, formic acid, or a formic acid salt is preferable. Further, two or more of these reducing agents can be used together.

As the solvent to be used in the reduction in a liquid phase, water is preferable, however, depending on dispersibility of a carrier, an organic solvent like an alcohol such as ethanol, 1-propanol, 2-propanol, n-butanol, or t-butanol; a ketone such as acetone, methyl ethyl ketone, methyl isobutyl ketone, or cyclohexanone; an organic acid such as acetic acid, n-valeric acid, or isovaleric acid; or a hydrocarbon such as heptane, hexane, or cyclohexane can be used alone or in combination of a plurality of these kinds. It is also possible to use a mixed solvent of water and these solvents.

In the case that the reducing agent is gas, it is preferable to carry out reduction in a pressure device such as an autoclave so as to increase the solubility of the gas into a solution. On this occasion, it is preferable to pressurize the inside of the pressure device with the reducing agent. The pressure is preferably 0.1 to 1 MPa (gauge pressure; hereinafter, pressure being expressed in gauge pressure).

Further, in the case that the reducing agent is a liquid, there is no limitation to a device for carrying out reduction and the reduction can be carried out by adding the reducing agent into a solution. The amount of the reducing agent is not particularly limited at this time, however, it is preferably 1 to 100 moles to 1 mole of palladium in its oxidized state.

The reduction temperature and the reduction time are variable depending on metal raw materials or metal oxides which are the objects to be reduced, reducing agents, and the like, however, the reduction temperature is preferably −5 to 150° C. and more preferably 15 to 80° C.

The reduction time is preferably 0.1 to 4 hours, more preferably 0.25 to 3 hours, and furthermore preferably 0.5 to 2 hours.

When a supported type catalyst is produced using metal raw materials to which reduction is not needed, the metal raw materials may be supported on the carrier on which the foregoing reduction has been carried out.

It is preferable to wash the resultant catalyst with water, an organic solvent, or the like. Through the washing with water, an organic solvent, or the like, impurities originated from metal raw materials such as chlorides, acetate group, nitrate group, or sulfate group, or those originated from reducing agents are removed. The washing method and the number of times of washing are not particularly limited, however, it is preferable to carry out the washing to the extent that the impurities can be sufficiently removed because it is apprehended that some impurities may impede the liquid-phase oxidation reaction. The catalyst washed may be directly used to the reaction after recovered by filtration, centrifugation, or the like. Further, in the case that a Pd reduction step and an Sb reduction step are carried out in separate steps, it is also preferable to carry out washing between the steps.

Further, the recovered catalyst may be dried. The drying method is not particularly limited, however, it is preferable to dry the recovered catalyst in air or in inert gas using dryer. It is also possible to activate the dried catalyst before it is used in the reaction, when it is needed. The method of activation is not particularly limited, however, for example, a method in which heat treatment of the catalyst is carried out under a reducing atmosphere of hydrogen flow can be listed. According to this method, oxide layer on the surface of palladium element or antimony element and impurities that has not been removed in washing can be removed.

(The Second Embodiment of the Palladium-Containing Catalyst)

The palladium-containing catalyst of the present invention is the one comprising palladium element which composes a metal, tellurium element, and bismuth element. The palladium-containing catalyst becomes capable of producing an α, β-unsaturated carboxylic acid in high selectivity from an olefin or an α, β-unsaturated aldehyde by causing the catalyst to have such a composition.

The fact that the palladium-containing catalyst comprises palladium element that composes a metal can be measured with XRD measurement, XPS (X ray photoelectron spectroscopy), and the like. In XRD measurement, there exists a peak corresponding to (111) face of palladium metal at about 40 degrees of X-ray diffraction angle (2θ) in an X-ray powder diffraction pattern using Cu—Kα line. This peak is usually observed at 40.11 degrees, however, it may shift toward lower angle by forming an alloy or an intermetallic compound between palladium element in its metallic state and tellurium element and/or bismuth element. In the present invention, it is defined that the catalyst comprises palladium element which composes a metal when a peak is observed at 39.0 degrees or above and 40.11 degrees or below as an X-ray diffraction angle (2θ). It is preferable that the palladium element which composes a metal be forming an alloy or an intermetallic compound with tellurium element and/or bismuth element as mentioned above, and it is more preferable that the catalyst comprise palladium element having the X-ray diffraction angle (2θ) of 39.2 degrees or above. Further, it is preferable that the catalyst comprise palladium element having the X-ray diffraction angle (2θ) of 40.0 degrees or below, and more preferable that the catalyst comprise palladium element having the X-ray diffraction angle (2θ) of 39.9 degrees or below.

The molar ratio of tellurium element to palladium element (Te/Pd) in the palladium-containing catalyst needs to exceed 0, and it is preferably 0.002 or more, and more preferably 0.003 or more, and the Te/Pd is preferably 0.30 or less, and more preferably 0.25 or less. The Te/Pd can be adjusted by a compounding ratio of each raw material of palladium element and tellurium element, which is used in the production of the palladium-containing catalyst as will be mentioned later.

The chemical state of tellurium element contained in the palladium-containing catalyst is not particularly limited and may be either a metallic state or an oxidized state, however, tellurium element is preferably in a metallic state because the electronic state of palladium element which composes a metal is more changed. Further, it is more preferable that tellurium element be forming an alloy or an intermetallic compound with palladium element because a proportion of palladium element, the electronic state of which has drastically changed, becomes high by being adjacent to tellurium element.

The molar ratio of bismuth element to palladium element (Bi/Pd) in the palladium-containing catalyst needs to exceed 0, and it is preferably 0.002 or more, and more preferably 0.003 or more, and the Bi/Pd is preferably 0.26 or less, more preferably 0.10 or less, and particularly preferably 0.06 or less. The Bi/Pd can be adjusted by a compounding ratio of each raw material of palladium element and bismuth element, which is used in the production of the palladium-containing catalyst as will be mentioned later.

The chemical state of bismuth element contained in the palladium-containing catalyst is not particularly limited and may be either a metallic state or an oxidized state, however, bismuth element is preferably in a metallic state because the electronic state of palladium element which composes a metal is more changed. Further, it is more preferable that bismuth element be forming an alloy or an intermetallic compound with palladium element because a proportion of palladium element, the electronic state of which has drastically changed, becomes high by being adjacent to bismuth element.

The sum of the Te/Pd and the Bi/Pd (i.e. (Te+Bi)/Pd) in the palladium-containing catalyst needs to exceed 0, and it is preferably 0.004 or more, and more preferably 0.006 or more, and preferably 0.4 or less, and more preferably 0.3 or less to more raise the selectivity to an α, β-unsaturated carboxylic acid and to more reduce the by-production of carbon dioxide.

The Te/Pd, Bi/Pd, and (Te+Bi)/Pd can be calculated from masses and atomic weights of palladium element, tellurium element, and bismuth element contained in the palladium-containing catalyst which has been prepared. The masses of palladium element, tellurium element, and bismuth element contained in the palladium-containing catalyst can be measured by the following method.

Preparation of a Treatment A Liquid:

In the case that the carrier contains silica, the palladium-containing catalyst, concentrated nitric acid, and 48% by mass fluoric acid are introduced into a Teflon (registered trademark) decomposition tube, and a dissolving treatment is carried out using a microwave digestion device. In the case that the carrier does not contain silica, the palladium-containing catalyst, concentrated nitric acid, concentrated sulfuric acid, and hydrogen peroxide aqueous solution are introduced into a Teflon (registered trademark) decomposition tube, and a dissolving treatment is carried out using a microwave digestion device. The resultant sample is filtrated and a filtrate and washing water after used in washing are gathered and filled up to a calibration mark on a measuring flask to make a treatment A liquid.

Preparation of a Treatment B Liquid:

In the case that there is insoluble residue in the foregoing treatment, a filter paper on which the insoluble residue has been gathered is transferred into a platinum crucible and is heated and burnt to ashes, and lithium metaborate is added to it and fused with a gas burner. After cooled, hydrochloric acid and a small amount of water are added to the crucible, and after the fused material is dissolved, the resultant solution is filled up to a calibration mark on a measuring flask to make a treatment B liquid.

Each mass of palladium element, tellurium element and bismuth element contained in the treatment A liquid and the treatment B liquid is determined quantitatively with ICP atomic emission spectrometer, and the mass of each element in the palladium-containing catalyst can be obtained from a sum of masses of each element in both the liquids.

The palladium-containing catalyst of the present invention may contain another metal element. For example, a noble metal element such as platinum, rhodium, ruthenium, iridium, gold, silver, or osmium; and a base metal element such as antimony, thallium, or lead can be listed. Two or more kinds of the other metal elements can also be included. From the viewpoint of realizing high catalyst activity, the total amount of palladium element, tellurium element, and bismuth element among the metal elements contained in the palladium-containing catalyst is preferably 50% by mass or more.

The palladium-containing catalyst of the present invention may be a nonsupported type, however, it is preferably a supported type in which palladium element, tellurium element, and bismuth element are supported on a carrier. As the carrier, for example, activated carbon, carbon black, silica, alumina, magnesia, calcia, titania or zirconia can be listed. Among them, silica, titania or zirconia is preferable. A preferable specific surface area of the carrier cannot be absolutely affirmed because it is variable depending on a kind of carrier and the like. In the case of silica, the specific surface area is preferably 50 $m^2/g$ or more and more preferably 100 $m^2/g$ or more, and preferably 1,500 $m^2/g$ or less and more preferably 1,000 $m^2/g$ or less. As the specific surface area of the carrier becomes smaller in the above range, a catalyst in which its useful components (palladium element, tellurium element, and bismuth element) are supported more on its surface can be produced, and as the specific surface area of the carrier becomes larger in the above range, a catalyst in which its useful components are supported more can be produced.

In the case of a supported type catalyst, a total loading ratio of palladium element, tellurium element, and bismuth element is preferably 0.1% by mass or more to the mass of the carrier before these elements are supported, more preferably 1% by mass or more, furthermore preferably 2% by mass or more, and particularly preferably 4% by mass or more, and preferably 40% by mass or less to the mass of the carrier before these elements are supported, more preferably 30% by mass or less, furthermore preferably 20% by mass or less, and particularly preferably 15% by mass or less.

The palladium-containing catalyst of the present invention can be produced using each metal of palladium element, tellurium element, and bismuth element, an alloy of these elements, or a compound containing these elements as a raw material. Among them, the compound containing these elements is preferable as a raw material because a high-activity catalyst in which useful components are highly dispersed on a carrier can be easily prepared.

The raw material of palladium element is not particularly limited and palladium metal, a palladium salt, a palladium oxide, or the like can be listed, however, among them, a palladium salt is preferable. As a palladium salt, for example, palladium chloride, palladium acetate, palladium nitrate, palladium sulfate, tetraamminepalladium chloride, or palladium bis (acetylacetonate) can be listed, and among them, palladium chloride, palladium acetate, palladium nitrate, or tetraamminepalladium chloride is preferable, and palladium nitrate is particularly preferable.

The raw material of tellurium element is not particularly limited and tellurium metal, a tellurium salt, telluric acid or its salt, tellurous acid or its salt, a tellurium oxide, or the like can be listed. As the tellurium salt, for example, hydrogen telluride, tellurium tetrachloride, tellurium dichloride, tellurium hexafluoride, tellurium tetraiodide, tellurium tetrabromide, or tellurium dibromide can be listed. As the tellurate, for example, sodium tellurate or potassium tellurate can be listed. As the tellurite, for example, sodium tellurite or potassium tellurite can be listed. Among them, telluric acid or its salt, tellurous acid or its salt, or a tellurium oxide is preferable.

The raw material of bismuth element is not particularly limited and bismuth metal, a bismuth salt, an organic bismuth compound, a bismuth oxide, or the like can be listed. As the bismuth salt, for example, bismuth(III) acetate, bismuth(III) acetate oxide, bismuth(III) bromide, basic bismuth(III) carbonate, bismuth(III) chloride, bismuth(III) fluoride, bismuth (III) iodide, basic bismuth(III) nitrate, bismuth(III) nitrate, bismuth(III) oxychloride, bismuth(III) phosphate, or bismuth (III) sulfate can be listed. As the organic bismuth compound, for example, triphenyl bismuth can be listed. Among them, the bismuth oxide or bismuth nitrate is preferable.

The foregoing raw materials of palladium element, tellurium element, and bismuth element are properly selected as the raw materials and used for producing the palladium-containing catalyst. The compounding ratios of these compounds are properly selected so that each molar ratio of palladium element, tellurium element and bismuth element in the palladium-containing catalyst becomes an objective value.

It is preferable to produce the palladium-containing catalyst by selecting a compound containing palladium element in an oxidized state, a compound containing tellurium element in an oxidized state, and a compound containing bismuth element in an oxidized state as raw materials of palladium element, tellurium element and bismuth element, respectively, and mixing them, and reducing the resultant mixture with a reducing agent.

Further, in the case of producing a supported type catalyst, it can be achieved by causing the foregoing raw materials to be supported on a carrier. The amount of the carrier to be used is properly selected so as to obtain a catalyst having an objective loading ratio.

The method for supporting the raw materials on a carrier is not particularly limited and, for example, a precipitation method, an ion-exchange method, an impregnation method, or a sedimentation method can be listed. In the case of the impregnation method, the raw materials of palladium element, tellurium element, and bismuth element may be simultaneously impregnated and supported, or any of the raw materials may be impregnated and supported, and then the rest of the raw materials may be impregnated and supported.

Further, it may be carried out, after supporting the raw materials of palladium element, tellurium element, and bismuth element on a carrier, to subject the resultant carrier to heat treatment to change it into the carrier on which palladium oxide, tellurium oxide, and bismuth oxide are supported. As the temperature range of the heat treatment, 200° C. or above is preferable and 300° C. or above is more preferable, and 800° C. or below is preferable and 700° C. or below is more preferable. The time of the heat treatment is not particularly limited, however, it is preferably within the range from 1 to 12 hours.

Subsequently, the palladium-containing catalyst is produced by reducing palladium element in its oxidized state, tellurium element in its oxidized state, and bismuth element in its oxidized state, which are supported on the carrier, with a reducing agent.

The reducing agent to be used is not particularly limited, and for example, hydrazine, formaldehyde, sodium borohydride, hydrogen, formic acid, a formic acid salt, ethylene, propylene, 1-butene, 2-butene, isobutylene, 1,3-butadiene, 1-heptene, 2-heptene, 1-hexene, 2-hexene, cyclohexene, allyl alcohol, methallyl alcohol, acrolein, or methacrolein can be listed. Two or more of these reducing agents can also be used together. When the reduction is carried out in a gas phase, hydrogen is preferable as a reducing agent. Further, when the reduction is carried out in a liquid phase, hydrazine, formaldehyde, formic acid, or a formic acid salt is preferable as a reducing agent.

As the solvent to be used in the reduction in a liquid phase, water is preferable, however, depending on dispersibility of a carrier in the case of a supported type catalyst, an organic solvent like an alcohol such as ethanol, 1-propanol, 2-propanol, n-butanol, or t-butanol; a ketone such as acetone, methyl ethyl ketone, methyl isobutyl ketone, or cyclohexanone; an organic acid such as acetic acid, n-valeric acid, or isovaleric acid; or a hydrocarbon such as heptane, hexane, or cyclohexane can be used alone or in combination of plurality of these kinds. It is also possible to use a mixed solvent of water and these solvents.

In the case that the reducing agent is a gas, it is preferable to carry out reduction in a pressure device such as autoclave so as to increase the solubility of the gas into a solution. On this occasion, the inside of the pressure device is pressurized with the reducing agent. The pressure is preferably 0.1 MPa or more and 1 MPa or less.

Further, in the case that the reducing agent is a liquid, there is no limitation to a device for carrying out reduction and the reduction can be carried out by adding the reducing agent into a solution. On this occasion, the amount of the reducing agent to be used is not particularly limited, however, it is preferably 1 mole or more and 100 moles or less to 1 mole of palladium in its oxidized state.

The reduction temperature and the reduction time are variable depending on reducing agents and the like, however, the reduction temperature is preferably −5° C. or above and more preferably 15° C. or above, and preferably 150° C. or below and more preferably 80° C. or below. The reduction time is preferably 0.1 hour or more, more preferably 0.25 hour or more, and furthermore preferably 0.5 hour or more, and preferably 4 hours or less, more preferably 3 hours or less, and furthermore preferably 2 hours or less.

It is preferable to wash the palladium-containing catalyst prepared by the reduction with water, a solvent, or the like. Through the washing with water, a solvent, or the like, impurities originated from raw materials such as chlorides, acetate group, nitrate group, or sulfate group, or those originated from reducing agents are removed. The washing method and the number of times of washing are not particularly limited, however, it is preferable to carry out the washing to the extent that the impurities can be sufficiently removed because it is apprehended that some impurities may impede the liquid-phase oxidation reaction of a olefin or an $\alpha$, $\beta$-unsaturated aldehyde. The catalyst washed may be directly used to the reaction after recovered by filtration, centrifugation, or the like.

Further, the recovered catalyst may be dried. The drying method is not particularly limited, however, usually the recovered catalyst is dried in air or in an inert gas using dryer. It is also possible to activate the dried catalyst before it is used in the liquid-phase oxidation reaction, when it is needed. The method of activation is not particularly limited, however, for example, a method in which heat treatment of the catalyst is carried out under a reducing atmosphere of hydrogen flow can be listed. According to this method, oxide layer on the surface of palladium element and impurities that has not removed in washing can be removed. The physical properties of the prepared catalyst can be confirmed with BET specific surface area measurement, XRD measurement, CO pulse adsorption method, TEM measurement, XPS measurement, and the like.

Metal palladium by itself exhibits an activity as an oxidation catalyst, however, it is not sufficient for the activity of the reaction of producing an $\alpha$, $\beta$-unsaturated carboxylic acid through oxidation of an olefin or an $\alpha$, $\beta$-unsaturated aldehyde and a large quantity of carbon dioxide as a by-product is formed. On the other hand, when bismuth element having a different electronegativity from that of palladium element is present, an electronic state of palladium element changes through the function of bismuth element. Further, when tellurium element having a different electronegativity from both of palladium element and bismuth element is present, an electronic state of palladium element further changes through the function of tellurium element. As a result, the activity of the main reaction in which an olefin or an $\alpha$, $\beta$-unsaturated aldehyde is oxidized to produce an $\alpha$, $\beta$-unsaturated carboxylic acid is raised while a side reaction in which carbon dioxide is formed is suppressed.

(Method for Producing an $\alpha$, $\beta$-Unsaturated Carboxylic Acid)

In the next place, a method for producing the $\alpha$, $\beta$-unsaturated carboxylic acid through liquid-phase oxidation of the olefin or the $\alpha$, $\beta$-unsaturated aldehyde with molecular oxygen using the palladium-containing catalyst of the present invention will be explained.

As the olefin which is a raw material, for example, propylene, isobutylene, or 2-butene can be listed, and among them, propylene or isobutylene is suitable. Two or more olefins can also be used together. The olefin which is a raw material may contain a small amount of a saturated hydrocarbon or a lower saturated aldehyde or both of them as impurities.

The $\alpha$, $\beta$-unsaturated carboxylic acid to be produced from the olefin is the one having the same carbon skeleton as the olefin has. Concretely, in the case that the raw material is propylene, acrylic acid is produced, and in the case that the raw material is isobutylene, methacrylic acid is produced. Further, usually, an $\alpha$, $\beta$-unsaturated aldehyde is simultaneously obtained from the olefin. The $\alpha$, $\beta$-unsaturated aldehyde has the same carbon skeleton as the olefin has. For example, in the case that the raw material is propylene, acrolein is obtained, and in the case that the raw material is isobutylene, methacrolein is obtained.

As the $\alpha$, $\beta$-unsaturated aldehyde which is a raw material, for example, acrolein, methacrolein, crotonaldehyde ($\beta$-methylacrolein), or cinnamaldehyde ($\beta$-phenylacrolein) can be listed. Among them, acrolein or methacrolein is suitable. Two or more $\alpha$, $\beta$-unsaturated aldehydes can also be used together. The $\alpha$, $\beta$-unsaturated aldehyde which is a raw material may contain a small amount of a saturated hydrocarbon or a lower saturated aldehyde or both of them as impurities.

The $\alpha$, $\beta$-unsaturated carboxylic acid to be produced from the $\alpha$, $\beta$-unsaturated aldehyde is the one in which the aldehyde group of the α, β-unsaturated aldehyde has changed into the carboxyl group. Concretely, in the case that the raw material is acrolein, acrylic acid is obtained, and in the case that the raw material is methacrolein, methacrylic acid is obtained.

As a raw material of the liquid-phase oxidation, either an olefin or an α, β-unsaturated aldehyde or a mixture of both of them may be used.

The liquid-phase oxidation reaction may be carried out by either a continuous type operation or a batch type operation, however, the continuous type operation is industrially preferable in consideration of the productivity.

The source of molecular oxygen to be used in the liquid-phase oxidation reaction is preferably air because it is economical, however, pure oxygen or a mixed gas of pure oxygen and air can be used, and if necessary, a diluted mixed gas in which air or pure oxygen is diluted with nitrogen, carbon dioxide or water vapor can also be used. It is preferable that such a molecular oxygen-containing gas be ordinarily supplied into a reaction vessel such as an autoclave under the pressurized state.

As the solvent to be used in the liquid phase oxidation reaction, for example, it is preferable to use at least one organic solvent selected from the group consisting of t-butanol, cyclohexanol, acetone, methyl ethyl ketone, methyl isobutyl ketone, acetic acid, propionic acid, n-butyric acid, isobutyric acid, n-valeric acid, isovaleric acid, ethyl acetate, and methyl propionate. Among them, at least one organic solvent selected from the group consisting of t-butanol, methyl isobutyl ketone, acetic acid, propionic acid, n-butyric acid, isobutyric acid, n-valeric acid, and isovaleric acid is more preferable. Further, it is preferable to cause water to coexist with the solvent to produce an α, β-unsaturated carboxylic acid in higher selectivity. The amount of water to coexist is not particularly limited, and it is preferably 2% by mass or more to the total mass of the solvent and water, and more preferably 5% by mass or more, and preferably 70% by mass or less, and more preferably 50% by mass or less. In the case of a mixed solvent of two or more kinds, the mixed solvent is preferably homogeneous, but it may be heterogeneous.

The total concentration of the olefin and the α, β-unsaturated aldehyde which are the raw materials of the liquid-phase oxidation reaction is preferably 0.1% by mass or more to the solvent existing in the reactor, and more preferably 0.5% by mass or more, and preferably 30% by mass or less, and more preferably 20% by mass or less.

The amount of the molecular oxygen to be used is preferably 0.1 mole or more to 1 mole of the total of the olefin and the α, β-unsaturated aldehyde which are the raw materials of the liquid-phase oxidation reaction, more preferably 0.2 mole or more, and furthermore preferably 0.3 mole or more, and preferably 20 moles or less, more preferably 15 moles or less, and furthermore preferably 10 moles or less.

It is preferable that the catalyst be used in a suspended state in the reaction liquid of the liquid-phase oxidation, however, the catalyst may be used in a fixed bed. The amount of the catalyst to be used is preferably 0.1% by mass or more to the liquid existing in the reactor, more preferably 0.5% by mass or more, and furthermore preferably 1% by mass or more, and preferably 30% by mass or less, more preferably 20% by mass or less, and furthermore preferably 15% by mass or less.

The reaction temperature and the reaction pressure are properly selected according to the solvent and the raw material to be used. The reaction temperature is preferably 30° C. or more, and more preferably 50° C. or more, and preferably 200° C. or less, and more preferably 150° C. or less. Further, the reaction pressure is preferably atmospheric pressure (0 MPa) or more, and more preferably 0.5 MPa or more, and preferably 10 MPa or less, and more preferably 5 MPa or less.

EXAMPLES

Hereinafter, the present invention will be more concretely explained by way of Examples and Comparative Examples, however, the present invention is not limited to these Examples. In the following Examples and Comparative Examples, "part(s)" means "part(s) by mass".
(XRD Measurement)

The measurement was performed with RU-200A (trade name) manufactured by Rigaku Corporation. The measuring conditions are: X-ray; Cu—Kα/40 kV/100 mA, Scan speed; 4°/min.
(Analysis of Raw Materials, Products, and By-Products in the Production of an α, β-Unsaturated Carboxylic Acid)

The analysis of raw materials, products, and by-products in the production of an α, β-unsaturated carboxylic acid was carried out using gas chromatography. Now, conversion of an olefin, selectivity to an α, β-unsaturated aldehyde to be produced, selectivity to an α, β-unsaturated carboxylic acid to be produced and selectivity to carbon dioxide to be produced as a by-product are defined in the following.

$$\text{Conversion of an olefin (\%)} = (B/A) \times 100$$

$$\text{Selectivity to an } \alpha, \beta\text{-unsaturated aldehyde (\%)} = (C/B) \times 100$$

$$\text{Selectivity to an } \alpha, \beta\text{-unsaturated carboxylic acid (\%)} = (D/B) \times 100$$

$$\text{Selectivity to carbon dioxide (\%)} = (E/B) \times 100$$

In these formulae, A represents number of moles of an olefin supplied, B represents number of moles of an olefin reacted, C represents number of moles of an α, β-unsaturated aldehyde produced, D represents number of moles of an α, β-unsaturated carboxylic acid produced, and E represents (number of moles of carbon dioxide produced as a by-product)/(number of carbon atoms in an olefin which is a raw material (4 in the case of isobutylene)).

Example 1

(Preparation of Catalyst)

To an aqueous solution obtained by dissolving 0.26 part of tartaric acid in 2.3 parts of pure water, 0.05 part of antimony oxide was dispersed and the resultant mixture was stirred for 30 minutes at 60° C. To the resultant homogeneous solution, 3.3 parts of palladium nitrate nitric acid solution (manufactured by Tanaka Kikinzoku International K.K., palladium element content: 22.65% by mass) was added, and to the resultant aqueous solution, pure water was further added to obtain, in all, 10.2 parts of the resultant solution. This solution was added to 15.0 parts of a particle silica carrier (specific surface area of 450 m²/g, pore volume of 0.68 cc/g, median diameter of 53.58 μm) little by little and the resultant mixture was shaken while these operations were repeated until the whole amount of the solution was added. The carrier on which the solution was impregnated with such a pore-filling method as described above was held at 100° C. in air for 3 hours, and calcined at 450° C. in air for 3 hours to obtain a silica carrier on which palladium element and antimony element were supported.

The silica carrier thus obtained was added to 40.0 parts of 37% by mass formaldehyde aqueous solution. Then a reduction treatment was carried out by heating the system to 70° C.

and keeping it at 70° C. for 2 hours while stirring. Then the system was filtrated under reduced pressure and filtrated while washed with 1,000 parts of hot water. Thereafter, the resultant system was dried at 100° C. for 2 hours under nitrogen flow to obtain a supported palladium-containing catalyst in which reduced palladium element and reduced antimony element were supported on the silica carrier. The Sb/Pd in the catalyst was 0.05. The loading ratio of palladium element was 5.0% by mass and the loading ratio of antimony element was 0.26% by mass in this catalyst. Here, a loading ratio means a ratio of a mass of each element to a mass of a carrier in a catalyst. In the XRD measurement of this catalyst, a peak was detected at around 2θ of 39.880 degrees.

In Examples 1 to 4 and Comparative Example 2, masses of palladium element, antimony element, and tellurium element, which were used in calculating Sb/Pd, Te/Pd, and a loading ratio of each element, were calculated from a palladium element content and a compounding amount of the raw material of palladium to be used, an antimony element content and a compounding amount of the raw material of antimony to be used, and a tellurium element content and a compounding amount of the raw material of tellurium to be used. The mass of the carrier in the catalyst was quantitatively determined as follows. At first, the catalyst was introduced into a platinum crucible and fused after sodium carbonate was added. Then, to the resultant mixture, distilled water was added to make a homogeneous solution and a quantitative determination of Si atom in the sample solution was carried out with ICP atomic emission spectrometry.

(Evaluation of Reaction)

Into an autoclave, 10.5 parts of the catalyst obtained by the above-mentioned method and 75 parts of 75% by mass t-butanol aqueous solution as a reaction solvent were introduced and the autoclave was shut tight. Subsequently, 2.0 parts of isobutylene was introduced into it, and the system was stirred (number of revolutions: 1,000 rpm) and heated to 90° C. After the heating was finished, nitrogen was introduced into the autoclave to the internal pressure of 2.4 MPa and then air was introduced into it to the internal pressure of 4.8 MPa and the reaction was started. Each time when the internal pressure dropped by 0.15 MPa the internal pressure: 4.65 MPa), oxygen was introduced into it by 0.15 MPa to adjust the internal pressure to 4.8 MPa (hereinafter, expressed also as "oxygen introduction operation"), and this operation was repeated 4 times during the reaction. The time taken from the start of the reaction to the first oxygen introduction operation was 4 minutes. After the fourth introduction of oxygen, when the internal pressure dropped to 4.65 MPa, the reaction was finished.

After the reaction was finished, the inside materials of the autoclave were cooled by putting the autoclave into an ice bath. A gas-sampling bag was attached to the gas outlet of the autoclave and the gas outlet was opened and the emerging gas was collected while the internal pressure of the reactor was released. The reaction liquid containing catalyst was taken out from the autoclave and the catalyst was separated by membrane filter and the reaction liquid was recovered. The recovered reaction liquid and the sampled gas were analyzed with gas chromatography and conversion and selectivity were calculated. The results are shown in Table 1.

Example 2

(Preparation of Catalyst)
Step 1:

To 3.3 parts of palladium nitrate nitric acid solution (manufactured by Tanaka Kikinzoku International K.K., palladium element content: 22.65% by mass), pure water was further added to obtain, in all, 10.2 parts of the resultant aqueous solution. This aqueous solution was added to 15.0 parts of a particle silica carrier, which is the same as that used in Example 1, little by little and the resultant mixture was shaken while these operations were repeated until the whole amount of the solution was added. The carrier on which the solution was impregnated by such a pore-filling method as described above was calcined at 450° C. in air for 3 hours to obtain a silica carrier on which palladium oxide was supported.

Step 2:

To 2.3 parts of pure water in which 0.52 part of tartaric acid was dissolved, 0.10 part of antimony oxide was dispersed and the resultant mixture was stirred for 30 minutes at 60° C. The homogeneous solution thus obtained was added to the silica carrier obtained in the step 1, on which palladium oxide was supported, little by little and the resultant mixture was shaken while these operations were repeated until the whole amount of the solution was added. A silica carrier containing palladium element and antimony element was obtained by impregnating the solution by such a pore-filling method as described above.

The silica carrier thus obtained was added to 40.0 parts of 37% by mass formaldehyde aqueous solution. Then a reduction treatment was carried out by heating the system to 70° C. and keeping it at 70° C. for 2 hours while stirring. Then the system was filtrated under reduced pressure and filtrated while washed with 1,000 parts of hot water. Thereafter, the resultant system was dried at 100° C. for 2 hours under nitrogen flow to obtain a supported palladium-containing catalyst in which reduced palladium element and reduced antimony element were supported on the silica carrier. The Sb/Pd in the catalyst was 0.10. The loading ratio of palladium element was 5.0% by mass and the loading ratio of antimony element was 0.53% by mass in this catalyst. In the XRD measurement of this catalyst, a peak was detected at around 2θ of 39.700 degrees.

(Evaluation of Reaction)

The same procedure of evaluation of reaction as in Example 1 was carried out except that 10.6 parts of the catalyst obtained by the above-mentioned method was used. The time taken from the start of the reaction to the first oxygen introduction operation was 3 minutes. The results are shown in Table 1.

Example 3

(Preparation of Catalyst)

The same procedure as in Example 1 was carried out except that the amount of antimony oxide used was changed to 0.15 part and the amount of tartaric acid used was changed to 0.78 part and a palladium-containing catalyst was obtained. The Sb/Pd in the catalyst was 0.15. The loading ratio of palladium element was 5.0% by mass and the loading ratio of antimony element was 0.79% by mass in this catalyst. In the XRD measurement of this catalyst, a peak was detected at around 2θ of 39.600 degrees.

(Evaluation of Reaction)

The same procedure of evaluation of reaction as in Example 1 was carried out using the catalyst obtained by the above-mentioned method. The time taken from the start of the reaction to the first oxygen introduction operation was 6 minutes. The results are shown in Table 1.

Example 4

(Preparation of Catalyst)

To 2.3 parts of pure water in which 0.30 part of tartaric acid was dissolved, 0.07 part of antimony oxide was dispersed and the resultant mixture was stirred for 30 minutes at 60° C. To the resultant homogeneous solution, 4.5 parts of palladium nitrate nitric acid solution (manufactured by Tanaka Kikinzoku Kogyo K.K., palladium element content: 22.65% by mass) was added. The resultant aqueous solution was added to 5.0 parts of a particle silica carrier (specific surface area of 450 $m^2$/g, pore volume of 0.68 cc/g, median diameter of 53.58 μm) little by little and the resultant mixture was shaken while these operations were repeated until the whole amount of the solution was added. The carrier on which the solution was impregnated by such a pore-filling method as described above was calcined at 450° C. in air for 3 hours to obtain a silica carrier on which palladium element and antimony element were supported.

The silica carrier thus obtained was added to 70 parts of 37% by mass formaldehyde aqueous solution. Then a reduction treatment was carried out by heating the system to 70° C. and keeping it at 70° C. for 2 hours while stirring. Then the system was filtrated under reduced pressure and filtrated while washed with 1,000 parts of hot water. After the washing, a silica carrier on which palladium element and antimony element subjected to reducing treatment were supported was obtained. Further, this silica carrier was dispersed in 50.0 parts of pure water, and a telluric acid aqueous solution obtained by dissolving 0.06 part of telluric acid in 5.0 parts of pure water was dropped to this dispersed solution thus obtained. Then a treatment was carried out by heating the system to 70° C. and keeping it at 70° C. for 2 hours while stirring. Then the system was filtrated under reduced pressure and filtrated while washed with 1,000 parts of hot water. Thereafter, the resultant system was dried at 100° C. for 2 hours under nitrogen flow to obtain a supported palladium-containing catalyst in which reduced palladium element, reduced antimony element, and reduced tellurium element were supported on the silica carrier. The Sb/Pd was 0.05 and Te/Pd was 0.05 in the catalyst. The loading ratio of palladium element was 20.0% by mass, the loading ratio of antimony element was 1.14% by mass, and the loading ratio of tellurium element was 1.20% by mass in this catalyst. In the XRD measurement of this catalyst, a peak was detected at around 2θ of 39.870 degrees.

(Evaluation of Reaction)

Into an autoclave, 3.0 parts of the catalyst obtained by the above-mentioned method and 75 parts of 75% by mass t-butanol aqueous solution as a reaction solvent were introduced and the autoclave was shut tight. Subsequently, 2.0 parts of isobutylene was introduced into it, and the system was stirred (number of revolutions: 1,000 rpm) and heated to 90° C. After the heating was finished, nitrogen was introduced into the autoclave to the internal pressure of 2.4 MPa and then air was introduced into it to the internal pressure of 4.8 MPa and the reaction was started. Each time when the internal pressure dropped by 0.10 MPa (the internal pressure: 4.70 MPa), oxygen was introduced into it by 0.10 MPa to adjust the internal pressure to 4.8 MPa (hereinafter, also expressed as "oxygen introduction operation"), and this operation was repeated 8 times during the reaction. The time taken from the start of the reaction to the first oxygen introduction operation was 2 minutes. After the eighth introduction of oxygen, when the internal pressure dropped to 4.70 MPa, the reaction was finished.

After the reaction was finished, the inside materials of the autoclave were cooled by putting the autoclave into an ice bath. A gas-sampling bag was attached to the gas outlet of the autoclave and the gas outlet was opened and the emerging gas was collected while the internal pressure of the reactor was released. The reaction liquid containing catalyst was taken out from the autoclave and the catalyst was separated by membrane filter and the reaction liquid was recovered. The recovered reaction liquid and the sampled gas were analyzed with gas chromatography and conversion and selectivity were calculated. The results are shown in Table 1.

Comparative Example 1

(Preparation of Catalyst)

To 2.16 parts of palladium nitrate solution (manufactured by N. E. Chemcat Corporation: nitric acid aqueous acidic solution containing 23.2% by mass palladium nitrate), pure water was further added to obtain, in all, 6.8 parts of the resultant solution. This solution was added to 10.0 parts of a particle silica carrier (specific surface area of 450 $m^2$/g, pore volume of 0.68 cc/g) little by little and the resultant mixture was shaken while these operations were repeated until the whole amount of the solution was added. The solution was thus impregnated to the carrier with such a pore-filling method as described above, and evaporation of the resultant carrier was carried out. Subsequently, calcination of the resultant carrier was carried out at 450° C. in air for 3 hours. The catalyst precursor thus obtained was added to 20 parts of 37% by mass formaldehyde aqueous solution. Then the system was heated to 70° C., kept at 70° C. for 2 hours while stirred, filtrated under reduced pressure and filtrated while washed with 1,000 parts of hot water to obtain a silica supported palladium-containing catalyst. The loading ratio of palladium element was 5.0% by mass in this catalyst. Here, a loading ratio means a ratio of a mass of each element to a mass of a carrier in a catalyst. In the XRD measurement of this catalyst, a peak was detected at 2θ of 39.48 degrees and it was confirmed that the catalyst contained palladium element which composed a metal.

In Examples 5 to 8, Comparative Example 1, and Comparative

Examples 3 to 5, Te/Pd, Bi/Pd, and a loading ratio of each element were calculated from masses and atomic weights of palladium element, tellurium element, and bismuth element contained in the catalyst after preparation, and a mass of a carrier. The masses of palladium element, tellurium element, and bismuth element contained in the catalyst were measured by the following method.

Preparation of a Treatment Liquid:

Into a Teflon (registered trademark) decomposition tube, 1 part of the catalyst, 50 parts of 62% by mass nitric acid aqueous solution, and 50 parts of 48% by mass hydrofluoric acid aqueous solution were introduced and a dissolving treatment was carried out using a microwave digestion device (MARS5 (trade name) manufactured by CEM Corporation).

Each mass of palladium element, tellurium element, and bismuth element contained in the homogeneous solution thus obtained was determined quantitatively with ICP atomic emission spectrometer (IRIS-Advantage (trade name) manufactured by Thermo Elemental Co., Ltd.), and each mass was estimated as the mass of each element in the catalyst. The mass of the carrier in the catalyst was quantitatively determined as follows. At first, the catalyst was introduced into a platinum crucible and fused after sodium carbonate was added. Then, to the resultant mixture, distilled water was added to make a homogeneous solution and a quantitative determination of Si atom in the sample solution was carried out with ICP atomic emission spectrometry.

(Evaluation of Reaction)

The total amount of the catalyst (0.5 part as palladium element) obtained by the above-mentioned method and 75 parts of 75% by mass t-butanol aqueous solution as a reaction solvent were introduced into an autoclave and the autoclave was shut tight. Subsequently, 2.0 parts of isobutylene was introduced into it, and the system was stirred (number of revolutions: 1,000 rpm) and heated to 90° C. After the heating was finished, nitrogen was introduced into the autoclave to the internal pressure of 2.4 MPa and then compressed air was introduced into it to the internal pressure of 4.8 MPa. When the internal pressure dropped by 0.15 MPa (the internal pressure: 4.65 MPa), oxygen was introduced into it by 0.15 MPa, and this operation was repeated during the reaction. The reaction was finished when the reaction time was 60 minutes.

After the reaction was finished, the inside of the autoclave was cooled by an ice bath. A gas-sampling bag was attached to the gas outlet of the autoclave and the gas outlet was opened and the emerging gas was collected while the internal pressure of the reactor was released. The reaction liquid containing catalyst was taken out from the autoclave and the catalyst was separated by membrane filter and the reaction liquid was recovered. The recovered reaction liquid and the sampled gas were analyzed with gas chromatography and conversion and selectivity were calculated. The results are shown in Table 1 and Table 2.

Comparative Example 2

(Preparation of Catalyst)

The same procedure as in Example 1 was carried out except that the amount of antimony oxide used was changed to 0.31 part and the amount of tartaric acid used was changed to 1.55 part and a palladium-containing catalyst was obtained. The Sb/Pd in the catalyst was 0.30. The loading ratio of palladium element was 5.0% by mass and the loading ratio of antimony element was 1.62% by mass in this catalyst. In the XRD measurement of this catalyst, a peak was detected at around 2θ of 39.500 degrees.

(Evaluation of Reaction)

The same procedure of evaluation of reaction as in Example 1 was carried out except that 10.7 parts of the catalyst obtained by the above-mentioned method was used. However, after the reaction was started, it took a longer time for the internal pressure to drop to reach 4.65 MPa, to be more precise, the time taken from the start of the reaction to the first oxygen introduction operation was 45 minutes. Consequently, the reaction was finished when 60 minutes had passed from the start of the reaction (oxygen introduction operation being only once), because it was understood that the catalyst had a lower activity than that of Example 1. The results are shown in Table 1.

TABLE 1

|  | Sb/Pd (molar ratio) | Te/Pd (molar ratio) | Reaction time (min) | Conversion of isobutylene (%) | Selectivity to methacrolein (%) | Selectivity to methacrylic acid (%) |
|---|---|---|---|---|---|---|
| Ex. 1 | 0.05 | 0 | 74 | 67.0 | 17.3 | 43.3 |
| Ex. 2 | 0.1 | 0 | 90 | 56.5 | 14.8 | 57.4 |
| Ex. 3 | 0.15 | 0 | 120 | 60.5 | 18.8 | 50.1 |
| Ex. 4 | 0.05 | 0.05 | 50 | 81.4 | 19.0 | 47.4 |
| Comp. Ex. 1 | 0 | 0 | 60 | 52.8 | 15.7 | 33.8 |
| Comp. Ex. 2 | 0.3 | 0 | 60 | 2.2 | 12.7 | 1.7 |

As illustrated above, an α,β-unsaturated carboxylic acid can be produced in higher selectivity by using the palladium-containing catalyst of the present invention.

Example 5

(Preparation of Catalyst)

To 0.0228 part of bismuth nitrate pentahydrate, 10 times the mass of bismuth nitrate pentahydrate of 62% by mass nitric acid aqueous solution was added to make a homogeneous solution. To this solution, 0.151 part of telluric acid and 10 times the mass of telluric acid of distilled water were added to make a homogeneous solution. To this solution, 2.16 parts of palladium nitrate solution (manufactured by N. E. Chemcat Corporation: nitric acid aqueous acidic solution containing 23.2% by mass palladium nitrate) was added and pure water was further added to obtain, in all, 6.8 parts of the resultant solution. This solution was added to 10.0 parts of a particle silica carrier (specific surface area of 450 m²/g, pore volume of 0.68 cc/g) little by little and the resultant mixture was shaken while these operations were repeated until the whole amount of the solution was added. The solution was thus impregnated to the carrier by such a pore-filling method as described above, and evaporation of the resultant carrier was carried out. Subsequently, calcination of the resultant carrier was carried out at 450° C. in air for 3 hours. The catalyst precursor thus obtained was added to 20 parts of 37% by mass formaldehyde aqueous solution.

Then the system was heated to 70° C., kept at 70° C. for 2 hours while stirred, filtrated under reduced pressure and filtrated while washed with 1,000 parts of hot water to obtain a silica supported palladium-containing catalyst. The Te/Pd was 0.14 and Bi/Pd was 0.01 in the catalyst. The loading ratio of palladium element was 5% by mass, the loading ratio of tellurium element was 0.84% by mass, and the loading ratio of bismuth element was 0.1% by mass in this catalyst. In the XRD measurement of this catalyst, a peak was detected at 2θ of 39.66 degrees and it was confirmed that the catalyst contained palladium element which composed a metal.

(Evaluation of Reaction)

The total amount of the catalyst (0.5 part as palladium element) obtained by the above-mentioned method and 75 parts of 75% by mass t-butanol aqueous solution as a reaction solvent were introduced into an autoclave and the autoclave was shut tight. Subsequently, 2.0 parts of isobutylene was introduced into it, and the system was stirred (number of revolutions: 1,000 rpm) and heated to 90° C. After the heating was finished, nitrogen was introduced into the autoclave to the internal pressure of 2.4 MPa and then compressed air was introduced into it to the internal pressure of 4.8 MPa. When the internal pressure dropped by 0.15 MPa (the internal pressure: 4.65 MPa), oxygen was introduced into it by 0.15 MPa, and this operation was repeated during the reaction. The reaction was finished when the reaction time was 60 minutes.

After the reaction was finished, the inside of the autoclave was cooled by an ice bath. A gas-sampling bag was attached to the gas outlet of the autoclave and the gas outlet was opened and the emerging gas was collected while the internal pressure of the reactor was released. The reaction liquid containing catalyst was taken out from the autoclave and the catalyst was separated by membrane filter and the reaction liquid was recovered. The recovered reaction liquid and the sampled gas were analyzed with gas chromatography and conversion and selectivity were calculated. The results are shown in Table 2.

Example 6

(Preparation of Catalyst)

The same procedure as in Example 5 was carried out except that the amount of bismuth nitrate pentahydrate used was changed to 0.0570 part and the amount of telluric acid used was changed to 0.135 part and a palladium-containing catalyst was obtained. The Te/Pd was 0.125 and Bi/Pd was 0.025 in the catalyst. The loading ratio of palladium element was 5% by mass, the loading ratio of tellurium element was 0.75% by mass, and the loading ratio of bismuth element was 0.25% by mass in this catalyst. In the XRD measurement of this catalyst, a peak was detected at 2θ of 39.50 degrees and it was confirmed that the catalyst contained palladium element which composed a metal.

(Evaluation of Reaction)

The same procedure of evaluation of reaction as in Example 5 was carried out using the catalyst obtained by the above-mentioned method. The results are shown in Table 2.

Example 7

(Preparation of Catalyst)

The same procedure as in Example 5 was carried out except that the amount of bismuth nitrate pentahydrate used was changed to 0.0912 part and the amount of telluric acid used was changed to 0.119 part and a palladium-containing catalyst was obtained. The Te/Pd was 0.11 and Bi/Pd was 0.04 in the catalyst. The loading ratio of palladium element was 5% by mass, the loading ratio of tellurium element was 0.66% by mass, and the loading ratio of bismuth element was 0.39% by mass in this catalyst. In the XRD measurement of this catalyst, a peak was detected at 2θ of 39.54 degrees and it was confirmed that the catalyst contained palladium element which composed a metal.

(Evaluation of Reaction)

The same procedure of evaluation of reaction as in Example 5 was carried out using the catalyst obtained by the above-mentioned method. The results are shown in Table 2.

Example 8

(Preparation of Catalyst)

The same procedure as in Example 5 was carried out except that the amount of bismuth nitrate pentahydrate used was changed to 0.114 part and the amount of telluric acid used was changed to 0.108 part and a palladium-containing catalyst was obtained. The Te/Pd was 0.10 and Bi/Pd was 0.05 in the catalyst. The loading ratio of palladium element was 5% by mass, the loading ratio of tellurium element was 0.6% by mass, and the loading ratio of bismuth element was 0.49% by mass in this catalyst. In the XRD measurement of this catalyst, a peak was detected at 2θ of 39.48 degrees and it was confirmed that the catalyst contained palladium element which composed a metal.

(Evaluation of Reaction)

The same procedure of evaluation of reaction as in Example 5 was carried out using the catalyst obtained by the above-mentioned method. The results are shown in Table 2.

Comparative Example 3

(Preparation of Catalyst)

The same procedure as in Example 5 was carried out except that the amount of bismuth nitrate pentahydrate used was changed to 0.114 part and telluric acid was not used, and a palladium-containing catalyst was obtained. The Bi/Pd in the catalyst was 0.05. The loading ratio of palladium element was 5% by mass and the loading ratio of bismuth element was 0.49% by mass in this catalyst. In the XRD measurement of this catalyst, a peak was detected at 2θ of 39.70 degrees and it was confirmed that the catalyst contained palladium element which composed a metal.

(Evaluation of Reaction)

The same procedure of evaluation of reaction as in Example 5 was carried out using the catalyst obtained by the above-mentioned method. The results are shown in Table 2.

Comparative Example 4

(Preparation of Catalyst)

The same procedure as in Example 5 was carried out except that, to 0.752 part of bismuth nitrate pentahydrate, 4 times the mass of bismuth nitrate pentahydrate of 62% by mass nitric acid aqueous solution was added to make a homogeneous solution, and further, telluric acid was not used, and a palladium-containing catalyst was obtained. The Bi/Pd in the catalyst was 0.33. The loading ratio of palladium element was 5% by mass and the loading ratio of bismuth element was 3.24% by mass in this catalyst. In the XRD measurement of this catalyst, a peak was detected at 2θ of 39.00 degrees and it was confirmed that the catalyst contained palladium element which composed a metal.

(Evaluation of Reaction)

The same procedure of evaluation of reaction as in Example 5 was carried out using the catalyst obtained by the above-mentioned method. The results are shown in Table 2.

Comparative Example 5

(Preparation of Catalyst)

The same procedure as in Example 5 was carried out except that bismuth nitrate pentahydrate was not used and the amount of telluric acid used was changed to 0.162 part, and a palladium-containing catalyst was obtained. The Te/Pd in the catalyst was 0.15. The loading ratio of palladium element was 5% by mass and the loading ratio of tellurium element was 0.9% by mass in this catalyst. In the XRD measurement of this catalyst, a peak was detected at 2θ of 39.20 degrees and it was confirmed that the catalyst contained palladium element which composed a metal.

(Evaluation of Reaction)

The same procedure of evaluation of reaction as in Example 5 was carried out using the catalyst obtained by the above-mentioned method. The results are shown in Table 2.

TABLE 2

| | Te/Pd (molar ratio) | Bi/Pd (molar ratio) | Conversion of iso-butylene (%) | Selectivity to methacrolein (%) | Selectivity to methacrylic acid (%) | Selectivity carbon to dioxide (%) |
|---|---|---|---|---|---|---|
| Ex. 5 | 0.14 | 0.01 | 68.0 | 21.6 | 46.1 | 2.8 |
| Ex. 6 | 0.125 | 0.025 | 77.1 | 19.8 | 51.8 | 2.4 |
| Ex. 7 | 0.11 | 0.04 | 68.9 | 29.2 | 45.3 | 2.9 |
| Ex. 8 | 0.10 | 0.05 | 72.1 | 25.0 | 46.3 | 3.8 |

TABLE 2-continued

| | Te/Pd (molar ratio) | Bi/Pd (molar ratio) | Conversion of iso-butylene (%) | Selectivity to meth-acrolein (%) | Selectivity to meth-acrylic acid (%) | Selectivity carbon to dioxide (%) |
|---|---|---|---|---|---|---|
| Comp. Ex. 1 | 0 | 0 | 52.8 | 15.7 | 33.8 | 6.0 |
| Comp. Ex. 3 | 0 | 0.05 | 56.8 | 21.5 | 39.3 | 4.6 |
| Comp. Ex. 4 | 0 | 0.33 | 20.1 | 17.2 | 0.6 | 4.3 |
| Comp. Ex. 5 | 0.15 | 0 | 67.8 | 17.3 | 44.5 | 5.5 |

As illustrated above, an α, β-unsaturated carboxylic acid can be produced in higher selectivity and a small amount of carbon dioxide was formed as a by-product by using the palladium-containing catalyst of the present invention.

What is claimed is:

1. A method for producing an α,β-unsaturated carboxylic acid, comprising:
   oxidizing at least one of an olefin and an α,β-unsaturated aldehyde with molecular oxygen in a liquid phase by contacting at least one of the olefin and the α,β-unsaturated aldehyde with the molecular oxygen in the presence of a palladium-containing catalyst comprising from 0.001 to 0.25 mole of antimony in a metallic state having 0 valence for 1 mole of palladium in a metallic state having 0 valence.

2. The method according to claim 1, wherein the palladium-containing catalyst further comprises 0.001 to 0.4 mole of tellurium for 1 mole of palladium.

* * * * *